(12) United States Patent
Bartsch et al.

(10) Patent No.: US 7,462,263 B2
(45) Date of Patent: Dec. 9, 2008

(54) METHOD FOR PURIFYING HYDROCYANIC ACID

(76) Inventors: Michael Bartsch, Konrad-Adenauer-Str. 38, Neustadt (DE) 67433; Robert Baumann, E 7, 23, Mannheim (DE) 68159; Gerd Haderlein, Hochgewanne 93a, Grünstadt (DE) 67269; Miquel Angel Flores, Acequia 27, Aranjuez (ES) 28300; Tim Jungkamp, Magnolialaan 19, Kapellen (BE) 2950; Hermann Luyken, Brüsseler Ring 34, Ludwigshafen (DE) 67069; Jens Scheidel, Ladenburger Strasse 35, Hirschberg (DE) 69493; Wolfgang Siegel, Goethestr. 34b, Limburgerhof (DE) 67117; Dagmar Pascale Kunsmann-Keitel, Goethestr. 34a, Limburgerhof (DE) 67117; Peter Bassler, Maria-Mandel-Str. 18, Viernheim (DE) 68519

( * ) Notice: Subject to any disclaimer, the term of this patent is extended or adjusted under 35 U.S.C. 154(b) by 581 days.

(21) Appl. No.: 10/553,537

(22) PCT Filed: Apr. 15, 2004

(86) PCT No.: PCT/EP2004/013973

§ 371 (c)(1),
(2), (4) Date: Oct. 17, 2005

(87) PCT Pub. No.: WO2004/092068

PCT Pub. Date: Oct. 28, 2004

(65) Prior Publication Data

US 2006/0201798 A1     Sep. 14, 2006

(30) Foreign Application Priority Data

Apr. 17, 2003   (DE)  ............................ 103 17 929

(51) Int. Cl.
*B01D 3/00* (2006.01)
*C01C 3/04* (2006.01)
*C07C 253/34* (2006.01)

(52) U.S. Cl. ............................ 203/12; 203/49; 203/71; 423/372; 558/338

(58) Field of Classification Search .................. 203/12, 203/49, 71, 100; 423/372; 558/335, 336, 558/338
See application file for complete search history.

(56) References Cited

U.S. PATENT DOCUMENTS

| | | | | |
|---|---|---|---|---|
| 1,934,838 A | * | 11/1933 | Andrussow | ................. 423/376 |
| 2,571,099 A | | 10/1951 | Arthur, Jr. et al. | |
| 3,329,582 A | | 7/1967 | Senneweld et al. | |
| 3,920,721 A | * | 11/1975 | Gosser | ....................... 558/339 |

FOREIGN PATENT DOCUMENTS

| | | |
|---|---|---|
| DE | 1 205 064 | 11/1965 |
| DE | 33 34 321 | 4/1985 |
| FR | 1377939 | 11/1964 |
| GB | 1 396 249 | 6/1975 |
| WO | WO-97/45369 | 12/1997 |

* cited by examiner

*Primary Examiner*—Virginia Manoharan
(74) *Attorney, Agent, or Firm*—Connolly Bove Lodge & Hutz LLP

(57) ABSTRACT

A process for dewatering hydrocyanic acid by distillation, which includes distilling crude hydrocyanic acid containing from 50 to 99.9% by weight of HCN, from 0.1 to 40% by weight of water, from 0 to 15% by weight of carbon oxides and optionally from 0.01 to 1% by weight of an involatile stabilizer, at a pressure of from 1 bar to 2.5 bar, a bottom temperature of from 100° C. to 130° C. and a top temperature of from 25° C. to 54° C., in the absence of a volatile stabilizer, in a distillation column to obtain a top draw stream containing purified, anhydrous hydrocyanic acid and carbon oxides and a bottom draw stream including water and, optionally, the involatile stabilizer.

9 Claims, No Drawings

METHOD FOR PURIFYING HYDROCYANIC ACID

RELATED APPLICATIONS

This application is a national stage application (under 35 U.S.C. 371) of PCT/EP2004/003973 filed Apr. 15, 2004 which claims benefit to German application 103 17 929.1 filed Apr. 17, 2003.

The invention relates to a process for purifying hydrocyanic acid by distillation, and also to a process for hydrocyanating olefins or dienes.

Hydrocyanic acid is prepared on the industrial scale by essentially three different processes. In a first process, hydrocyanic acid is obtained by ammoxidizing methane with oxygen and ammonia (Andrussow process). In a second process, hydrocyanic acid is obtained from methane and ammonia by ammodehydrogenation in the absence of oxygen (BMA process of Degussa). Finally, hydrocyanic acid can be obtained on the industrial scale by dehydrating formamide (BASF process).

In all of the aforementioned processes, the gaseous reaction effluent is condensed. The condensate may contain water. An acidic stabilizer, for example $SO_2$, sulfuric acid, phosphoric acid or acetic acid is added to the condensate in order to prevent the autocatalytic polymerization of hydrocyanic acid which can lead to blockages in pipelines.

Hydrocyanic acid is used on the industrial scale to hydrocyanate olefins or dienes to the corresponding nitrites. The hydrocyanation is typically carried out in the presence of a nickel(0) catalyst, for example tetrakis(triethyl phosphite) nickel(0) or tetrakis(tri-p-tolyl phosphite)nickel(0). This nickel(0) catalyst is very sensitive toward protic compounds such as water and acid. For instance, the presence of water in the hydrogen cyanide used considerably reduces the yield of adiponitrile in the hydrocyanation of butadiene. The hydrocyanic acid used should therefore be substantially water- and acid-free.

U.S. Pat. No. 2,571,099 describes a process for preparing nitrites by hydrocyanating conjugated diolefins (dienes) in the presence of a nickel carbonyl catalyst. In the process, the highest yields are achieved when the hydrocyanic acid used is at least partly dried. According to this document, substantially anhydrous hydrocyanic acid is obtained by treating the anhydrous hydrocyanic acid with a dehydrating agent.

Volatile acidic stabilizers are at least partly removed by passing a nitrogen stream through the hydrocyanic acid for a few minutes.

The use of dehydrating agents, for example molecular sieves, is laborious and expensive. They have to be contacted with the aqueous hydrocyanic acid, then removed again from the dewatered hydrocyanic acid and finally regenerated.

It is an object of the present invention to provide a simpler process for dewatering hydrocyanic acid.

We have found that this object is achieved by a process for dewatering hydrocyanic acid by distillation, which comprises distilling crude hydrocyanic acid containing from 50 to 99.9% by weight of HCN, from 0.1 to 40% by weight of water, from 0 to 15% by weight of carbon oxides and optionally from 0.01 to 1% by weight of an non-volatile stabilizer, at a pressure of from 1 bar to 2.5 bar, a bottom temperature of from 100° C. to 130° C. and a top temperature of from 25° C. to 54° C., in the absence of a volatile stabilizer, in a distillation column to obtain a top draw stream comprising purified, anhydrous hydrocyanic acid and carbon oxides and a bottom draw stream comprising water and, where appropriate, the non-volatile stabilizer.

Surprisingly, despite the comparatively high temperatures in the distillation column and even though no volatile stabilizer is used, no polymerization of hydrocyanic acid occurs during distillation. In this context, it has to be considered that, in the case of the possible use of non-volatile stabilizers, they remain in the column bottom and therefore cannot have stabilizing action in the distillation column above the feed of the crude hydrocyanic acid.

The process according to the invention achieves simple dewatering of the aqueous crude hydrocyanic acid by distillation. The addition of expensive dehydrating agents such as molecular sieves can therefore be dispensed with. Even non-volatile stabilizers are also removed directly in this way.

Suitable non-volatile stabilizers which may be present in the crude hydrocyanic acid to be dewatered are, for example, sulfuric acid and phosphoric acid. These may be present in the crude hydrocyanic acid instead of volatile stabilizers, for example sulfur dioxides. It is thus also unnecessary to remove volatile stabilizers, for example by passing inert gas through the hydrocyanic acid before it is used in the hydrocyanation reaction, as described in U.S. Pat. No. 2,571,099.

The crude hydrocyanic acid to be dewatered by the process according to the invention contains from 50 to 99.9% by weight, preferably from 70 to 95% by weight, of HCN, from 0.1 to 40% by weight, preferably from 5 to 30% by weight, of water, from 0 to 15% by weight, preferably from 0.1 to 10% by weight, of carbon oxides (CO and $CO_2$) and, if desired, from 0.01 to 1% by weight of an non-volatile stabilizer.

An anhydrous hydrocyanic acid having a water content of generally <100 ppm, preferably <10 ppm is obtained.

The process may also be carried out when the crude hydrocyanic acid to be dewatered contains no stabilizer at all (i.e. no non-volatile stabilizer either).

When the crude hydrocyanic acid contains non-volatile stabilizer, they are preferably phosphoric acid or sulfuric acid.

The process according to the invention may be carried out in a customary distillation column. Preference is given to bubble-cap tray columns or columns having structured packing.

The process according to the invention is preferably carried out to dewater aqueous crude hydrocyanic acid, as obtained in the thermal cleavage of formamide.

It has also been found that the anhydrous hydrocyanic acid obtained by the process according to the invention can be stored directly over a prolonged period even in the absence of a stabilizer. The resulting anhydrous hydrocyanic acid can thus be stored at a temperature of from 5 to 25° C. over a period of from 2 to 10 days or even longer, for example a period of 5 days, without polymerization of hydrocyanic acid occurring. This is especially significant if the dewatered hydrocyanic acid is to be stored intermediately in a buffer vessel before its further use in a hydrocyanation reaction.

When a buffer vessel is provided, it is preferably the reflux vessel of the column, to which the condensed top draw stream is fed and from which the reflux is withdrawn which is designed as a buffer vessel.

Carbon oxides which are distilled overhead with the hydrocyanic acid can be stripped out in a downstream purifying column with an inert gas, typically nitrogen.

The anhydrous hydrocyanic acid obtained may subsequently be used to hydrocyanate olefins or dienes to the corresponding nitriles.

The invention thus also provides a process for hydrocyanating olefins or dienes by a) in a first step, distilling and thus dewatering crude hydrocyanic acid containing from 50 to 99.9% by weight of HCN, from 0.1 to 40% by weight of water, from 0 to 15% by weight of carbon oxides and optionally from 0.01 to 1% by weight of an non-volatile stabilizer, at a pressure of from 1 bar to 2.5 bar, a bottom temperature of from 100° C. to 130° C. and a top temperature of from 25° C. to 54° C., in the absence of a volatile stabilizer, in a distillation column, and optionally storing the dewatered hydrocyanic acid obtained as a top draw stream in the absence of a stabilizer, and b) reacting the purified, anhydrous hydrocyanic acid in the absence of a stabilizer with the olefin or diene in the presence of a hydrocyanation catalyst.

The hydrocyanation of olefins and dienes is generally carried out in the presence of catalysts based on phosphine, phosphite and phosphinite complexes of nickel or of palladium, as described in "Applied Homogenous Catalysis with Organometallic Compounds", Volume 1, VCH Weinheim, p. 465 ff. To prepare adiponitrile by hydrocyanating butadiene, nickel(0) phosphite catalysts are used predominantly, optionally in the presence of a Lewis acid such as metal salts or triphenylboron as a promoter. The reaction is effected in the liquid phase in a solvent, for example tetrahydrofuran, at a temperature in the range from 30 to 150° C.

The invention is illustrated in detail by the examples which follow.

EXAMPLES

Example 1

Distillation of Hydrocyanic Acid in the Presence of an Non-volatile Stabilizer

A bubble-cap tray column having a diameter of 30 mm and a tray number of 37 is charged continuously with 65 g/h of crude hydrocyanic acid containing 99.6% by weight of HCN, 0.2% by weight of water and 0.2% by weight of phosphoric acid as an non-volatile stabilizer. The column is operated at a pressure of 1.2 bar absolute. At this pressure, a temperature of 32° C. is established at the top of the column and a temperature of 107° C. at the bottom of the column. The top stream of anhydrous hydrocyanic acid is continuously withdrawn and collected in a buffer vessel. The hydrocyanic acid withdrawn at the top of the column is clear and colorless; its water content is measured by IR spectrometry and is below the detection limit of 50 ppm. The bottom stream consists of water, high-boiling phosphoric acid and traces of HCN (in the ppm range).

The distillation could be operated stably over a period of months without formation of deposits or blockages as a result of polymer hydrocyanic acid.

Example 2

Distillation of Hydrocyanic Acid Without Stabilizer

In a continuously operated experimental apparatus, HCN is obtained by gas phase dehydration of formamide. After condensation of unconverted formamide and removal of the ammonia by-product by acidic washing from the reaction effluent of the formamide dehydration, a crude hydrocyanic acid use stream composed of 24.9 kg/h of HCN, 6.7 kg/h of water, 1.25 kg/h of $CO_2$ and 1.7 kg/h of CO is obtained and is fed into the HCN rectification column. The HCN rectification column has a diameter of 100 mm and a length of 12 m and contains a sheet metal packing corresponding to 25 theoretical plates. The crude hydrocyanic acid is fed at the height of the 12th theoretical plate. The water is removed at the bottom of the column; the bottom temperature is 100° C. The top draw stream consists of anhydrous HCN having a water content of <10 ppm, CO and $CO_2$. The top temperature is 23° C. The top draw stream is condensed and fed into a downstream hydrocyanation reactor.

We claim:

1. A process for dewatering hydrocyanic acid by distillation, which comprises distilling crude hydrocyanic acid containing from 50 to 99.9% by weight of HCN, from 0.1 to 40% by weight of water, from 0 to 15% by weight of carbon oxides and optionally from 0.01 to 1% by weight of an non-volatile stabilizer, at a pressure of from 1 bar to 2.5 bar, a bottom temperature of from 100° C. to 130° C. and a top temperature of from 25° C. to 54° C., in the absence of a volatile stabilizer, in a distillation column to obtain a top draw stream containing purified, anhydrous hydrocyanic acid and carbon oxides and a bottom draw stream comprising water and, optionally, the non-volatile stabilizer.

2. A process according to claim 1, wherein the crude hydrocyanic acid comprises, as an non-volatile stabilizer, phosphoric acid or sulfuric acid.

3. A process according to claim 1, wherein the crude hydrocyanic acid contains no involatile stabilizer.

4. A process according to claim 1, wherein the obtained purified, anhydrous hydrocyanic acid has a water content of<100 ppm.

5. A process according to claim 1, wherein the distillation column is a bubble-cap tray column or column having structured packing.

6. A process according to claim 1, wherein the crude hydrocyanic acid is obtained by thermally cleaving formamide.

7. A process according to claim 1, wherein the carbon oxides present in the purified, anhydrous hydrocyanic acid are stripped out using an inert gas in a downstream purification column.

8. A process according to claim 1, wherein the anhydrous hydrocyanic acid is stored at from 5 to 25° C. in the absence of a stabilizer over a period of from 2 to 10 days.

9. A process for hydrocyanating olefins or dienes by
a) in a first step, dewatering crude hydrocyanic acid by a process according to claim 1 and optionally storing it in the absence of a stabilizer,
b) reacting the anhydrous hydrocyanic acid in the absence of a stabilizer with the olefin or diene in the presence of a hydrocyanation catalyst.

* * * * *

UNITED STATES PATENT AND TRADEMARK OFFICE
CERTIFICATE OF CORRECTION

PATENT NO.        : 7,462,263 B2                                       Page 1 of 1
APPLICATION NO.   : 10/553537
DATED             : December 9, 2008
INVENTOR(S)       : Michael Bartsch et al.

It is certified that error appears in the above-identified patent and that said Letters Patent is hereby corrected as shown below:

Title Page, Item (86)
In the PCT Application No. reads "PCT No. PCT/EP2004/013973" and should read --PCT No. PCT/EP2004/003973--

Signed and Sealed this

Thirty-first Day of March, 2009

JOHN DOLL
*Acting Director of the United States Patent and Trademark Office*